US012766310B2

(12) United States Patent
Reynolds et al.

(10) Patent No.: US 12,766,310 B2
(45) Date of Patent: Oct. 20, 2026

(54) CIRCULATORY SUPPORT DEVICE WITH STEERABLE CANNULA

(71) Applicant: Boston Scientific Scimed Inc., Maple Grove, MN (US)

(72) Inventors: Brian Reynolds, Ramsey, MN (US); Darrin Dale Beekman, Osseo, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 718 days.

(21) Appl. No.: 18/118,537

(22) Filed: Mar. 7, 2023

(65) Prior Publication Data

US 2023/0285741 A1 Sep. 14, 2023

Related U.S. Application Data

(60) Provisional application No. 63/317,725, filed on Mar. 8, 2022.

(51) Int. Cl.
*A61M 60/867* (2021.01)
*A61M 25/00* (2006.01)
(Continued)

(52) U.S. Cl.
CPC .......... *A61M 60/867* (2021.01); *A61M 60/13* (2021.01); *A61M 60/174* (2021.01);
(Continued)

(58) Field of Classification Search
CPC .. A61M 60/867; A61M 60/237; A61M 60/13; A61M 60/174; A61M 60/857;
(Continued)

(56) References Cited

U.S. PATENT DOCUMENTS

| | | | |
|---|---|---|---|
| 5,527,159 A | 6/1996 | Bozeman, Jr. et al. | |
| 5,692,882 A | 12/1997 | Bozeman, Jr. et al. | |

(Continued)

FOREIGN PATENT DOCUMENTS

| | | | |
|---|---|---|---|
| EP | 847767 B1 | 2/2005 | |
| EP | 2155037 B1 * | 4/2017 | ......... A61B 1/00071 |

(Continued)

OTHER PUBLICATIONS

US 9,067,007 B2, 06/2015, Tanner et al. (withdrawn)

(Continued)

*Primary Examiner* — Lindsey G Wehrheim
(74) *Attorney, Agent, or Firm* — Seager, Tufte & Wickhem LLP

(57) ABSTRACT

A percutaneous circulatory support device includes a housing, an impeller disposed within the housing and being rotatable relative to the housing, through the housing, and out of the outlet, a cannula coupled to the housing, the cannula having a body extending between a proximal end and a distal end and along a longitudinal axis, a structural body portion, a surface coating disposed onto the structural body portion of the cannula, and a channel defined between the structural body portion of the cannula and the surface coating, and a pull wire coupled to the cannula and extending through the channel of the cannula. Manipulation of the pull wire causes a change in shape profile of the cannula body.

19 Claims, 5 Drawing Sheets

(51) Int. Cl.

| | |
|---|---|
| ***A61M 25/01*** | (2006.01) |
| ***A61M 60/13*** | (2021.01) |
| ***A61M 60/174*** | (2021.01) |
| ***A61M 60/237*** | (2021.01) |
| ***A61M 60/857*** | (2021.01) |

(52) U.S. Cl.

CPC ........ *A61M 60/237* (2021.01); *A61M 60/857* (2021.01); *A61M 25/0045* (2013.01); *A61M 25/005* (2013.01); *A61M 25/0108* (2013.01); *A61M 25/0147* (2013.01); *A61M 2205/0266* (2013.01)

(58) Field of Classification Search

CPC ............ A61M 25/0045; A61M 25/005; A61M 25/0108; A61M 25/0147; A61M 2205/0266

See application file for complete search history.

(56) References Cited

U.S. PATENT DOCUMENTS

| | | | | |
|---|---|---|---|---|
| 5,947,892 | A | 9/1999 | Benkowski et al. | |
| 6,135,729 | A | 10/2000 | Aber | |
| 6,139,487 | A | 10/2000 | Siess | |
| 6,176,822 | B1 | 1/2001 | Nix et al. | |
| 6,544,216 | B1 | 4/2003 | Sammler et al. | |
| 7,841,976 | B2 | 11/2010 | McBride et al. | |
| 7,927,068 | B2 | 4/2011 | McBride et al. | |
| 7,972,122 | B2 | 7/2011 | Larose et al. | |
| 8,376,707 | B2 | 2/2013 | McBride et al. | |
| 8,591,393 | B2 | 11/2013 | Walters et al. | |
| 8,597,170 | B2 | 12/2013 | Walters et al. | |
| 8,684,904 | B2 | 4/2014 | Campbell et al. | |
| 8,721,517 | B2 | 5/2014 | Zeng et al. | |
| 8,992,163 | B2 | 3/2015 | McBride et al. | |
| 9,050,418 | B2 * | 6/2015 | Schima | A61M 60/178 |
| 9,072,825 | B2 | 7/2015 | Pfeffer et al. | |
| 9,138,518 | B2 | 9/2015 | Yuen et al. | |
| 9,162,017 | B2 | 10/2015 | Evans et al. | |
| 9,308,302 | B2 | 4/2016 | Zeng | |
| 9,308,304 | B2 | 4/2016 | Peters et al. | |
| 9,327,067 | B2 | 5/2016 | Zeng et al. | |
| 9,364,592 | B2 | 6/2016 | McBride et al. | |
| 9,364,593 | B2 | 6/2016 | McBride et al. | |
| 9,381,288 | B2 | 7/2016 | Schenck et al. | |
| 9,421,311 | B2 | 8/2016 | Tanner et al. | |
| 9,446,179 | B2 | 9/2016 | Keenan et al. | |
| 9,675,740 | B2 | 6/2017 | Zeng et al. | |
| 9,717,833 | B2 | 8/2017 | McBride et al. | |
| 9,770,543 | B2 | 9/2017 | Tanner et al. | |
| 9,872,947 | B2 | 1/2018 | Keenan et al. | |
| 9,895,476 | B2 | 2/2018 | Larose et al. | |
| 9,907,890 | B2 | 3/2018 | Muller | |
| 9,956,332 | B2 | 5/2018 | Larose et al. | |
| 9,962,475 | B2 | 5/2018 | Yuen et al. | |
| 9,964,115 | B2 | 5/2018 | Scheckel | |
| 10,029,037 | B2 | 7/2018 | Muller et al. | |
| 10,039,872 | B2 | 8/2018 | Zeng et al. | |
| 10,071,192 | B2 | 9/2018 | Zeng | |
| 10,086,121 | B2 | 10/2018 | Fitzgerald et al. | |
| 10,105,475 | B2 | 10/2018 | Muller | |
| 10,117,980 | B2 | 11/2018 | Keenan et al. | |
| 10,149,932 | B2 | 12/2018 | McBride et al. | |
| 10,215,187 | B2 | 2/2019 | McBride et al. | |
| 10,232,099 | B2 | 3/2019 | Peters et al. | |
| 10,251,985 | B2 | 4/2019 | Larose et al. | |
| 10,251,986 | B2 | 4/2019 | Larose et al. | |
| 10,279,095 | B2 | 5/2019 | Aboul-Hosn et al. | |
| 10,478,539 | B2 | 11/2019 | Pfeffer et al. | |
| 10,478,540 | B2 | 11/2019 | Scheckel et al. | |
| 10,525,178 | B2 | 1/2020 | Zeng | |
| 10,576,192 | B2 | 3/2020 | Muller et al. | |
| 10,576,193 | B2 | 3/2020 | Tanner et al. | |
| 10,709,829 | B2 | 7/2020 | Muller | |
| 10,709,830 | B2 | 7/2020 | Tanner et al. | |
| 10,765,789 | B2 | 9/2020 | Zeng et al. | |
| 10,780,208 | B2 | 9/2020 | Siess et al. | |
| 10,786,610 | B2 | 9/2020 | Zeng | |
| 10,799,624 | B2 | 10/2020 | Pfeffer et al. | |
| 10,842,921 | B2 | 11/2020 | Siess et al. | |
| 10,864,308 | B2 | 12/2020 | Muller et al. | |
| 10,864,309 | B2 | 12/2020 | McBride et al. | |
| 10,874,783 | B2 | 12/2020 | Pfeffer et al. | |
| 10,894,115 | B2 | 1/2021 | Pfeffer et al. | |
| 10,918,774 | B2 | 2/2021 | Stanfield et al. | |
| 10,960,116 | B2 | 3/2021 | Yuen et al. | |
| 10,980,927 | B2 | 4/2021 | Pfeffer et al. | |
| 11,058,865 | B2 | 7/2021 | Fitzgerald et al. | |
| 11,123,539 | B2 | 9/2021 | Pfeffer et al. | |
| 11,129,978 | B2 | 9/2021 | Pfeffer et al. | |
| 11,167,124 | B2 | 11/2021 | Pfeffer et al. | |
| 11,227,986 | B2 | 1/2022 | Male et al. | |
| 11,235,138 | B2 | 2/2022 | Gross-Hardt et al. | |
| 11,253,693 | B2 | 2/2022 | Pfeffer et al. | |
| 11,260,213 | B2 | 3/2022 | Zeng et al. | |
| 11,273,301 | B2 | 3/2022 | Pfeffer et al. | |
| 11,311,712 | B2 | 4/2022 | Zeng et al. | |
| 11,338,214 | B2 | 5/2022 | White et al. | |
| 11,357,967 | B2 | 6/2022 | Zeng et al. | |
| 11,400,276 | B2 | 8/2022 | Chopra et al. | |
| 11,497,896 | B2 | 11/2022 | Tanner et al. | |
| 11,517,736 | B2 | 12/2022 | Earles et al. | |
| 11,583,659 | B2 | 2/2023 | Pfeffer et al. | |
| 11,628,294 | B2 | 4/2023 | Chopra et al. | |
| 11,708,833 | B2 | 7/2023 | McBride et al. | |
| 11,754,075 | B2 | 9/2023 | Schuelke et al. | |
| 11,786,700 | B2 | 10/2023 | Pfeffer et al. | |
| 2005/0209557 | A1 * | 9/2005 | Carroll | A61M 25/0138 604/95.04 |
| 2008/0114339 | A1 | 5/2008 | McBride et al. | |
| 2009/0060743 | A1 | 3/2009 | McBride et al. | |
| 2013/0303831 | A1 | 11/2013 | Evans | |
| 2013/0331639 | A1 | 12/2013 | Campbell et al. | |
| 2017/0296725 | A1 | 10/2017 | Peters et al. | |
| 2018/0110908 | A1 * | 4/2018 | Larose | A61M 60/148 |
| 2018/0303990 | A1 | 10/2018 | Siess et al. | |
| 2018/0311423 | A1 | 11/2018 | Zeng et al. | |
| 2020/0237982 | A1 | 7/2020 | Tuval et al. | |
| 2021/0015982 | A1 | 1/2021 | Kerkhoffs et al. | |
| 2021/0038785 | A1 | 2/2021 | Siess et al. | |
| 2021/0106810 | A1 | 4/2021 | Pfeffer et al. | |
| 2021/0268264 | A1 | 9/2021 | Stotz et al. | |
| 2022/0134082 | A1 | 5/2022 | Pfeffer et al. | |

FOREIGN PATENT DOCUMENTS

| | | | | |
|---|---|---|---|---|
| EP | 2301598 B1 | | 7/2017 | |
| EP | 3352808 B1 | | 9/2023 | |
| WO | WO-2005123169 A1 | * | 12/2005 | A61B 1/00071 |

OTHER PUBLICATIONS

International Search Report and Written Opinion for International Application No. PCT/US2023/014724, dated Jun. 13, 2023. (17 pages.).

* cited by examiner

CIRCULATORY SUPPORT DEVICE WITH STEERABLE CANNULA

CROSS-REFERENCE TO RELATED APPLICATIONS

This application claims priority to U.S. Provisional Application No. 63/317,725, filed Mar. 8, 2022, which is herein incorporated by reference in its entirety.

TECHNICAL FIELD

The present disclosure relates to a steerable cannula for a percutaneous circulatory support device. More specifically, the present disclosure relates to a steerable cannula having pull wires for use with a percutaneous circulatory support device.

BACKGROUND

Percutaneous circulatory support devices such as blood pumps can provide transient support for up to approximately several weeks in patients with compromised heart function or cardiac output. Several issues may complicate delivery and operation of blood pumps within the heart, including difficulty with guidewire advancement, trauma to cardiac tissue, and oscillation and/or migration of the blood pump resulting in decreased performance of the blood pump. In some embodiments, increasing the control with which the blood pump can be steered, tracked and/or positioned may be desired.

SUMMARY

In an Example 1, a percutaneous circulatory support device includes a housing, an impeller disposed within the housing and being rotatable relative to the housing, through the housing, and out of the outlet, a cannula coupled to the housing, the cannula having a body extending between a proximal end and a distal end and along a longitudinal axis, a structural body portion, a surface coating disposed onto the structural body portion of the cannula, and a channel defined between the structural body portion of the cannula and the surface coating, and a pull wire coupled to the cannula and extending through the channel of the cannula. Manipulation of the pull wire causes a change in shape profile of the cannula body.

In an Example 2, the device of Example 1 includes wherein the device includes two pull wires.

In an Example 3, the device of Example 2 includes wherein the cannula body is defined by a longitudinal axis, and the two pull wires are coupled to the cannula body on opposing sides of the cannula body relative to the longitudinal axis.

In an Example 4, the device of any one of Examples 1-3 further includes wherein the surface coating is composed of a polymer coating.

In an Example 5, the device of any one of Examples 1-4 further includes wherein the pull wire is composed of nitinol.

In an Example 6, the device of any one of Examples 1-5 further includes wherein the pull wire comprises a radiopaque coating.

In an Example 7, the device of any one of Examples 1-6 further includes wherein the cannula body is formed of a plurality of wires in a braided configuration.

In an Example 8, the device of any one of Examples 1-6 further includes wherein the body of the cannula is composed of a plurality of wires in a helical configuration.

In an Example 9, a percutaneous circulatory support device includes a housing, an impeller disposed within the housing and being rotatable relative to the housing, a cannula coupled to the housing, the cannula having a body extending between a proximal end and a distal end along a longitudinal axis, a first pull wire coupled to the body of the cannula on a first side of the cannula, and a second pull wire coupled to the body of the cannula on a second side of the cannula. Manipulation of the first and second pull wires causes a change in a configuration of the cannula body.

In an Example 10, the device of Example 9 further includes wherein the first side is opposite the second side relative to the longitudinal axis.

In an Example 11, the device of Example 9 or Example 10 further includes wherein the cannula body comprises a structural body portion and a surface coating disposed on the structural body portion.

In an Example 12, the device of Example 11 further includes wherein the cannula comprises a channel defined between the structural body portion and the surface coating configured to receive at least one pull wire.

In an Example 13, a method for positioning a blood pump within a subject, the blood pump including a cannula having a body extending along a longitudinal axis and a pull wire coupled the body, includes advancing the blood pump through the vasculature of the subject, manipulating the pull wire to cause a change in a shape profile of the cannula, crossing the aortic valve of the subject with the blood pump such that the cannula is at least partially positioned in the left ventricle of the subject, and manipulating the pull wire to cause a change in a shape of the cannula body.

In an Example 14, the method of Example 13 further includes wherein manipulating the pull wire includes retracting the pull wire in a proximal direction.

In an Example 15, the method of Example 13 or Example 14 further includes wherein prior to the manipulating of the pull wire, the cannula body extends along the longitudinal axis.

In an Example 16, a percutaneous circulatory support device includes a housing including an outlet, an impeller disposed within the housing and being rotatable relative to the housing to cause blood to flow through the housing and out of the outlet, a cannula coupled to the housing, the cannula having a body extending between a proximal end and a distal end and along a longitudinal axis, a structural body portion, a surface coating disposed onto the structural body portion of the cannula, and a channel defined between the structural body portion of the cannula and the surface coating, and a pull wire coupled to the cannula and extending through the at least one channel of the cannula. Manipulation of the pull wire causes a change in shape profile of the cannula body.

In an Example 17, the device of Example 16 includes wherein the device comprises two pull wires.

In an Example 18, the device of Example 17 includes wherein the cannula body is defined by a longitudinal axis, and the two pull wires are coupled to the cannula body on opposing sides of the cannula body relative to the longitudinal axis.

In an Example 19, the device of Example 16 further includes wherein the surface coating is composed of a polymer coating.

In an Example 20, the device of Example 16 further includes wherein the pull wire is composed of nitinol.

In an Example 21, the device of Example 16 further includes wherein the a pull wire comprises a radiopaque coating.

In an Example 22, the device of Example 16 further includes wherein the cannula body is formed of a plurality of wires in a braided configuration.

In an Example 23, the device of Example 16 further includes wherein the body of the cannula is composed of a plurality of wires in a helical configuration.

In an Example 24, the device of Example 16 further includes wherein manipulation of the pull wire causes the cannula body to have a curved profile.

In an Example 25, the device of Example 24 further includes wherein the manipulation of the pull wire includes retracting the pull wire in a proximal direction.

In an Example 26, the device of Example 16 further includes wherein the channel is positioned on an interior surface of the structural body portion.

In an Example 27, the device of Example 16 further includes wherein the channel is positioned on an exterior surface of the structural body portion.

In an Example 28, a percutaneous circulatory support device includes a housing, an impeller disposed within the housing and being rotatable relative to the housing, a cannula coupled to the housing, the cannula having a body extending between a proximal end and a distal end along a longitudinal axis, a first pull wire coupled to the body of the cannula on a first side of the cannula, and a second pull wire coupled to the body of the cannula on a second side of the cannula. Manipulation of the first and second pull wires causes a change in a configuration of the cannula body.

In an Example 29, the device of Example 28 further includes wherein the first side is opposite the second side relative to the longitudinal axis.

In an Example 30, the device of Example 28 further includes wherein the cannula body includes a structural body portion and a surface coating disposed on the structural body portion.

In an Example 31, the device of Example 28 further includes wherein the cannula comprises a channel defined between the structural body portion and the surface coating configured to receive at least one pull wire.

In an Example 32, a method for positioning a blood pump within a subject, the blood pump including a cannula having a body extending along a longitudinal axis and a pull wire coupled the body, includes advancing the blood pump through the vasculature of the subject, manipulating the pull wire to cause a change in a shape profile of the cannula, crossing the aortic valve of the subject with the blood pump such that the cannula is at least partially positioned in the left ventricle of the subject, and manipulating the pull wire to cause a change in a shape of the cannula body.

In an Example 33, the method of Example 32 further includes wherein manipulating the pull wire includes retracting the pull wire in a proximal direction.

In an Example 34, the method of Example 32 further includes wherein prior to the manipulating of the pull wire, the cannula body extends along the longitudinal axis.

In an Example 35, the method of Example 34 further includes wherein after the manipulating of the pull wire, the cannula body comprises a curved profile.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Figure 1:
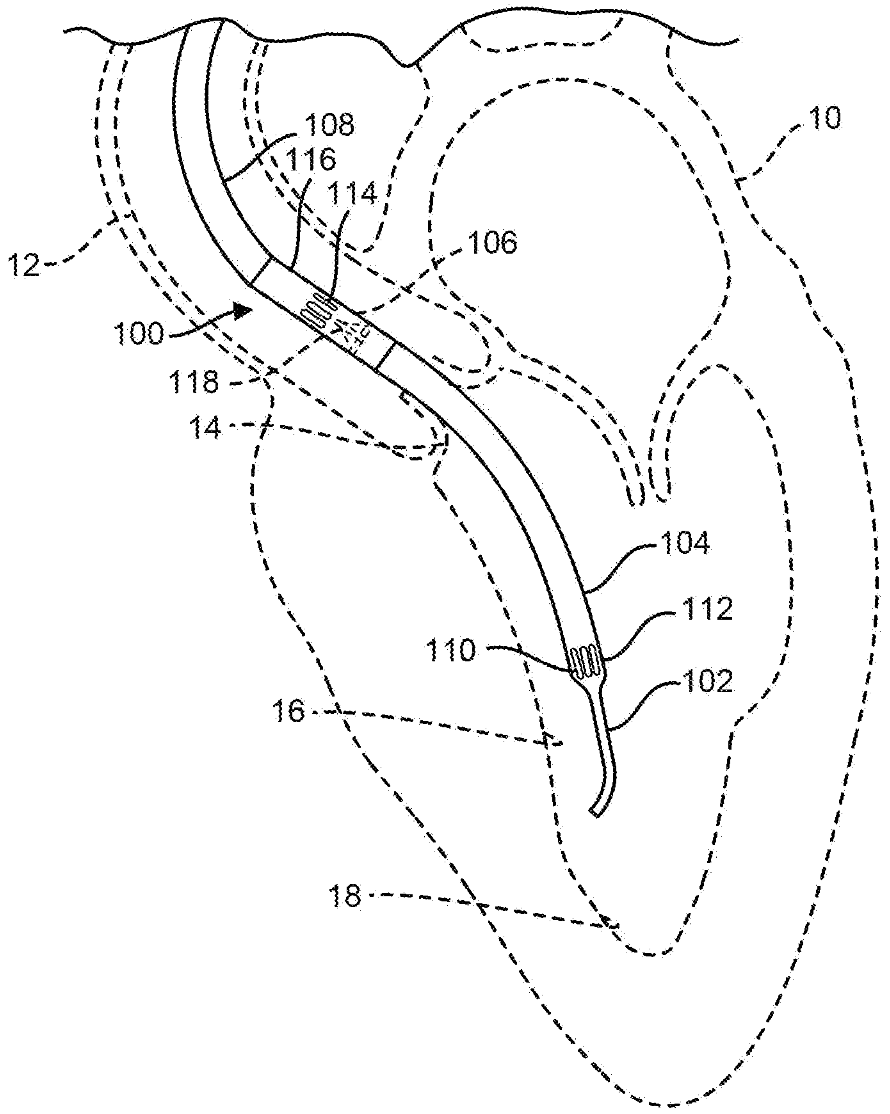
FIG. 1 illustrates a percutaneous circulatory support device after delivery into a patient's heart, in accordance with embodiments of the present disclosure.

FIG. 1 depicts a portion of an illustrative percutaneous mechanical circulatory support device 100 (also referred to herein, interchangeably, as a "blood pump"), and its relative position in a human heart 10, in accordance with embodiments of the subject matter disclosed herein. The blood pump 100 may be delivered percutaneously, for example, by passing the blood pump 100 through the vasculature, through the aorta 12, and then positioning the blood pump 100 within the heart 10 with respect to the aortic valve 14 and the left ventricle 16, as shown in FIG. 1. In some embodiments and as described in further detail below, the blood pump 100 may provide enhanced trackability and steering control and may be delivered without using an ancillary guidewire (not shown), that is a guidewire separate from the blood pump 100. Alternatively, the blood pump 100 may be delivered using an ancillary guidewire.

With continued reference to FIG. 1, the blood pump 100 generally includes a flexible distal tip portion 102, a cannula 104, an impeller portion 106, and a catheter 108. The cannula 104 may have a flexible construction to facilitate delivery of the blood pump 100. The cannula 104 includes one or more blood inlets 110 located on a distal portion 112 thereof, and one or more blood outlets 114 are located on a housing 116 of the impeller portion 106. The housing 116 carries an impeller 118, and the impeller 118 rotates relative to the housing 116 to cause blood to flow into the inlets 110, through the housing 116, and out of the outlets 114. During operation and as shown in FIG. 1, the blood pump 100 may be positioned within the heart 10 such that the inlets 110 are positioned in the left ventricle 16 and the outlets 114 are positioned in the aorta 12. As a result, rotation of the impeller 118 relative to the housing 116 causes blood to flow from the left ventricle 16, through the cannula 104 and the impeller portion 106, and into the aorta 12. In some cases, during operation the blood pump 100 may be positioned such that the flexible distal tip portion 102 is located in close proximity of, or in contact with, the wall of the left ventricle 16, for example, in the location of the apex 18 of the left ventricle 16.

Figure 2A:
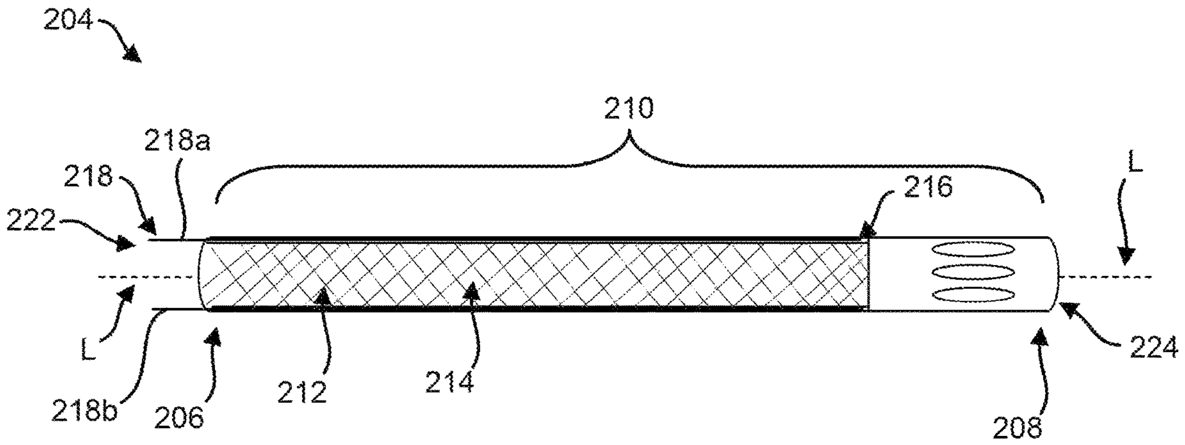
FIG. 2A illustrates a cross sectional view of a cannula in a first configuration, in accordance with embodiments of the present disclosure.

FIG. 2A illustrates an embodiment of a cannula 204 that may be used with the above-described blood pump 100. The cannula 204 comprises a proximal end 206 and a distal end 208 and extends along a longitudinal axis L. Further, the cannula 204 comprises a body 210 extending between the proximal end 206 and the distal end 208. As illustrated, the body 210 is composed of a structural body portion 212 and a surface coating 214 disposed onto the structural body portion 212. The structural body portion 212 may be composed of a plurality of wires configured to form a braided wire structure. In other embodiments, the plurality of wires may be configured for defining a helical configuration for the structural body portion 212. The wire of the structural body portion 212 may be nitinol, allowing for a memory shape configuration. However, the wire may be composed of various other materials, for example stainless steel or another low carbon alloy. In other embodiments, the structural body portion 212 may also be comprised of a slotted tube. The tube may be made from metals such as nitinol or stainless steel or polymers such as polycarbonate, polyamide, or polyetheretherketone (PEEK). The slots may be created with a laser cutting process or cutting blades. The structural body portion 212 is also configured such that the cannula 204 is flexible and may bend and/or rotate. Further, as previously disclosed, the structural body portion 212 is covered by the surface coating 214. In other words, the surface coating may be disposed onto the surfaces, including the exterior and/or interior surfaces, of the structural body portion 212. The surface coating 214 may be disposed onto the structural body portion 212 by various methods, for example dipping the structural body portion 212 into the surface coating 214, spraying the surface coating 214 onto the structural body portion 212, forming a polymer over the structural body portion 212 with a heat process, or through various other applicable methods. In various embodiments, the surface coating 214 is a film that is adhered onto the structural body portion 212. The surface coating 214 may be composed of various types of material, for example a polymer coating or a silicone coating. In other embodiments the surface coating 214 is an outer layer applied with a polymer reflow process and made from a polymer such as polyurethane or polyether block amide. The surface coating 214 may be beneficial for at least reducing the friction that may occur between the structural body portion 212 and the other components of the blood pump 100 or the vasculature of the subject. The surface coating 214 may also be configured for minimizing a coefficient of friction between the wires of the structural body portion 212 and any media, for example blood, that is being received by the cannula 204.

As illustrated in FIG. 2A, the cannula 204 may additionally comprise at least one channel 216 that is defined between the structural body portion 212 and the surface coating 214. More specifically, the channel 216 may be a pathway that is positioned on an exterior surface of the structural body portion 212 and internally to the surface coating 214 of the cannula 204. However, in various other embodiments, such as the alternative embodiment illustrated in FIG. 2B, the channel 216 may be a pathway that is positioned internally of the structural body portion 212. In this way, the channel 216 extends within a lumen of the cannula 204 between the surface coating 214 and an interior surface of the structural body portion 212.

Figure 2B:
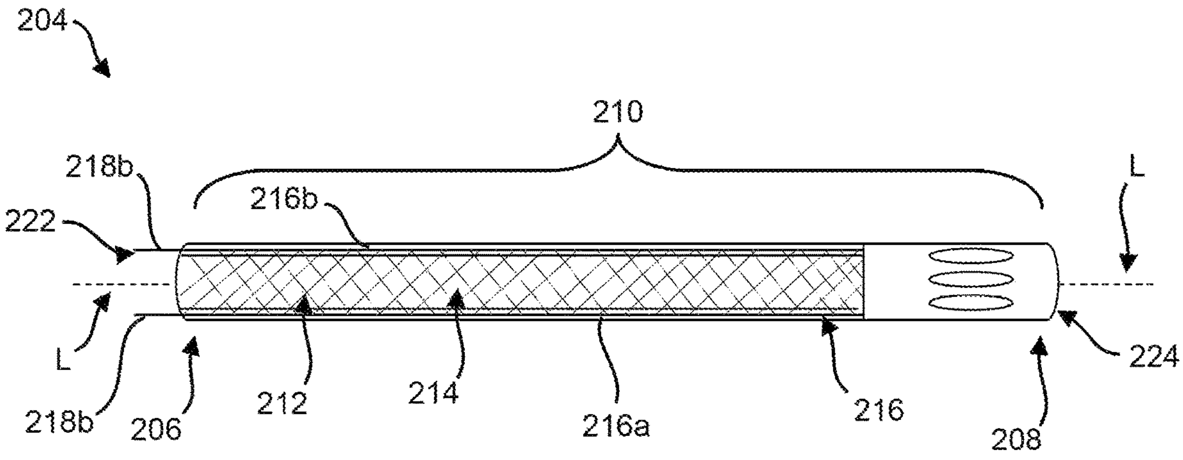
FIG. 2B illustrates a cross sectional view of a cannula in a first configuration, in accordance with embodiments of the present disclosure.

In some embodiments, for example as illustrated in FIG. 2B, the cannula 204 may comprise a first channel 216*a* and a second channel 216*b*. The channels 216*a*, 216*b* may be configured for receiving at least one pull wire 218, illustratively a first pull wire 218*a* and a second pull wire 218*b*. However, in various other embodiments any number of channels and/or pull wires may be incorporated. For example, the cannula 204 may include three or more pull wires and the channel 216 may include three or more channels.

In some embodiments, the first pull wire 218*a* and the second pull wire 218*b* extend through the first channel 216*a* and the second channel 216*b*, respectively, from the proximal end 206 to the distal end 208 of the cannula 204. The first pull wire 218*a* and the second pull wire 218*b* may be coupled to the structural body portion 212 of the body 210. More specifically, the first pull wire 218*a* and the second pull wire 218*b* may be welded or otherwise mechanically coupled to wires of the structural body portion 212. In other embodiments, the first pull wire 218*a* and the second pull wire 218*b* may embedded within the surface coating 214 of the body 210. Various other methods of coupling the first pull wire 218*a* and the second pull wire 218*b* to the cannula 204 may be incorporated as well, and the above-described examples are not meant to be limiting. As illustrated, the first channel 216*a* and first pull wire 218*a* may be positioned on a first side 222 of the cannula 204, while the second channel 216*b* and the second pull wire 218*b* are positioned on a second side 224 of the cannula 204. As illustrated, the first side 222 and the second side 224 are opposite from one another relative to the longitudinal axis L. However, various other configurations of the first and second pull wires 218*a*, 218*b* may be incorporated. Additionally, in some embodiments, at least one pull wire 218 comprises a radiopaque coating. This radiopaque coating may include barium, platinum, or tungsten. This may aid the operator understanding the positioning of the cannula 204 during the delivery of the blood pump 100 with the use of an imaging system.

Figure 3:
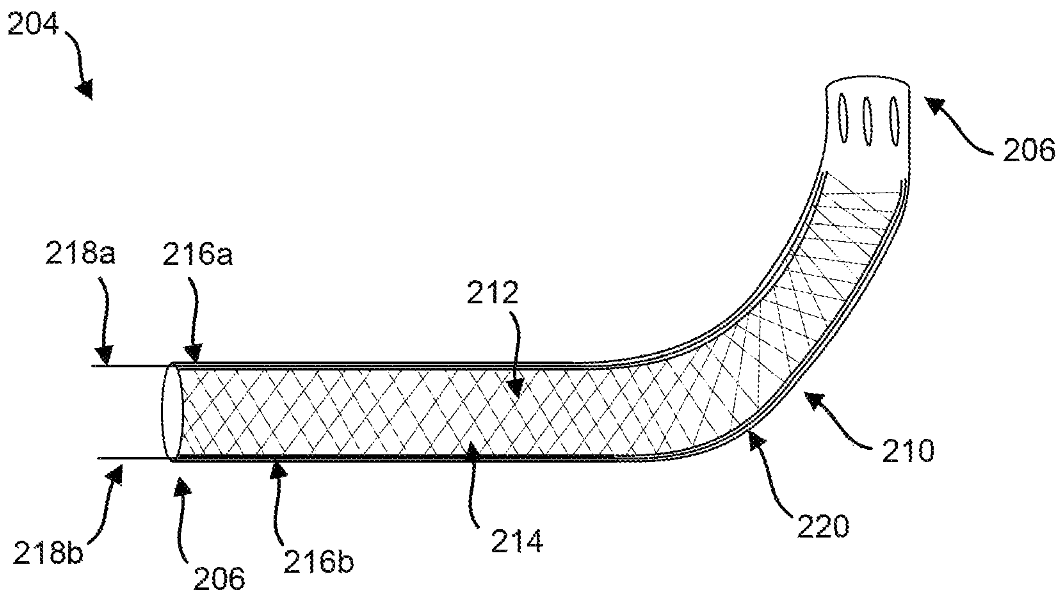
FIG. 3 illustrates a cross sectional view of the cannula of FIG. 2A in a second configuration, in accordance with embodiments of the present disclosure.

In various embodiments, the first pull wire 218*a* and the second pull wire 218*b* extend from the cannula 204, through the catheter 108 (FIG. 1) and through a handle of the catheter 108 so that the operator is able to manipulate the pull wires 218*a*, 218*b*. More specifically, the operator or physician may apply tension through pulling the pull wires 218*a*, 218*b* (i.e., retracting the ends of the pull wires 218*a*, 218*b* proximally) and release the tension through releasing the pull wires 218*a*, 218*b*. As will be described further herein, due to the positioning of the pull wires 218*a*, 218*b* and the flexibility of the body 210, the manipulation of the pull wires 218*a*, 218*b* causes a change in a shape profile or configuration of the cannula 204. For example, FIG. 2A illustrates an initial configuration of the cannula 204. This configuration may be prior to any manipulation of at least one pull wire 218. The cannula 204 extends along the longitudinal axis L and has a generally linear shape profile. FIG. 3 illustrates the cannula 204 after manipulation of at least one pull wire 218.

More specifically, FIG. 3 illustrates the cannula 204 with the body 210 having a second configuration, and more specifically, a configuration defined by the body 210 having a curved profile. In this way, the proximal end 206 maintains an extension along the longitudinal axis L, however, the distal end 208 is now altered to be directed toward a direction approximately perpendicular with the longitudinal axis L. In other words, the body 210 comprises a curved profile such that it comprises a bend 220 having a radius of curvature. The bend 220 as illustrated in FIG. 3 is provided as an example, and in other embodiments the bend 220 may have a larger and/or a smaller radius of curvature. The value of the radius of curvature may be dictated by the amount of tension that is added to the pull wire 218 by the operator. In this way, the operator is directly in control of the extent of the curvature of the body 210 of the cannula 204 to allow for increased patient or subject customization. Additionally, the position of the bend 220 along the cannula 204 may be varied. For example, the bend 220 may be closer to the distal end 208 and/or the proximal end 206 of the cannula 204 than is shown in FIG. 3. In embodiments wherein the structural body portion 212 comprises a helical configuration, manipulation of at least one pull wire 218 may cause rotation of the body 210 of the cannula 204.

Figure 4:
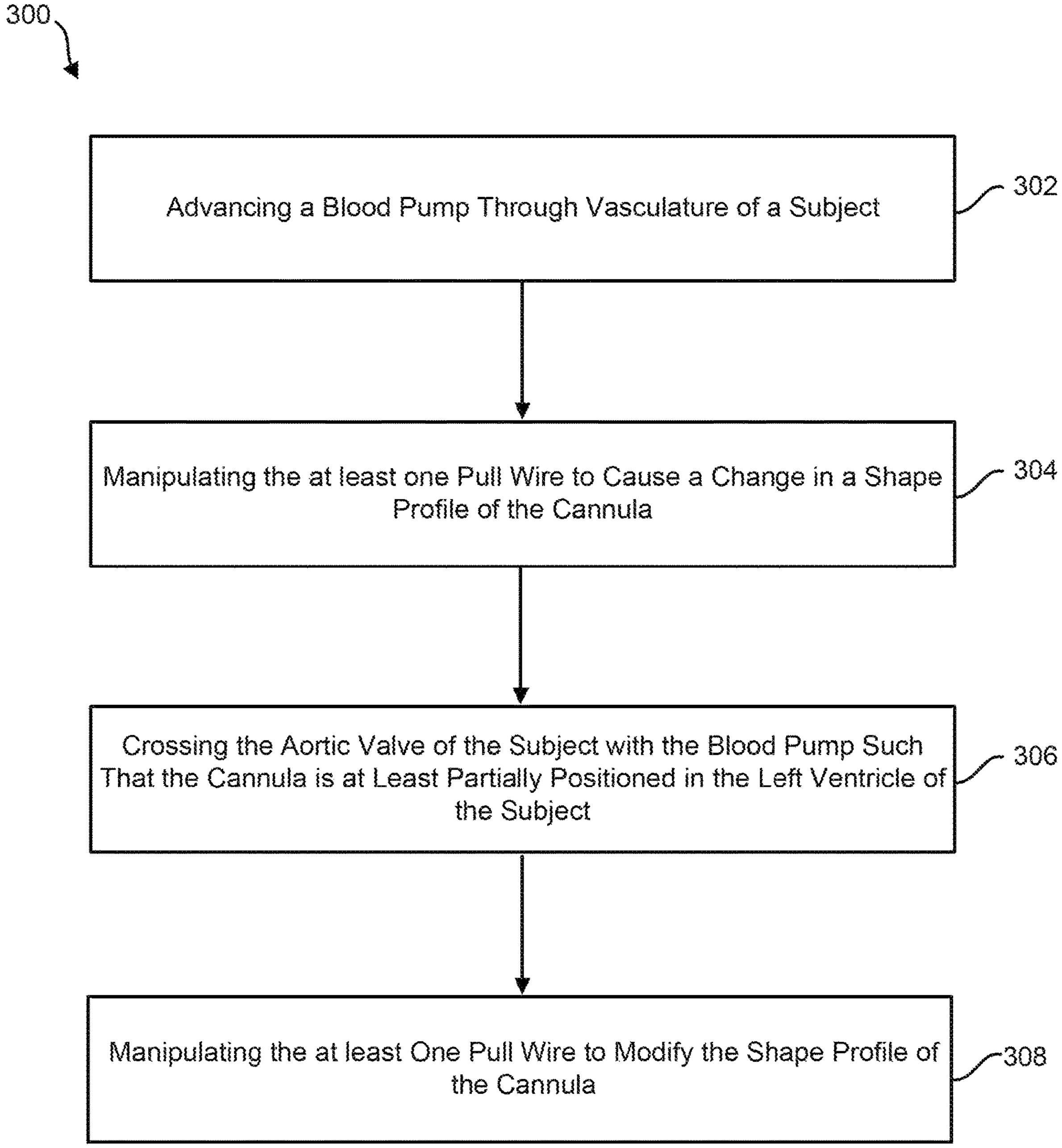
FIG. 4 illustrates a flow chart illustrating a method for positioning a blood pump, in accordance with embodiments of the present disclosure.

FIG. 4 illustrates a flow chart for a method 300 for positioning the blood pump 100 within a subject, the blood pump 100 comprising the cannula 204. At block 302, the method includes advancing the blood pump 100 through the vasculature of the subject. At block 304, the method further includes manipulating the pull wire 218 to cause a change in shape of the cannula 204. In various embodiments, the manipulating of the pull wire 218 includes manipulating the first pull wire 218*a* and the second pull wire 281*b*. More specifically, manipulation causes a shape profile of the body 210 of the cannula 204 to change. For example, the body 210 may change from the generally linear shape profile shown in FIG. 2A, to the generally curved profile shown in FIG. 3. As previously described, manipulating the pull wire 218 may include retracting the pull wire 218 in the proximal direction, or applying tension to the pull wire. However, various other methods may be used for manipulating the pull wire 218. For example, the handle of the catheter 108 may include retaining mechanisms for moving and/or positioning the pull wire 218 into a desired position steering the cannula 204 and controlling the shape profile of the cannula 204.

At block 306, the method 300 further includes crossing the aortic valve of the subject with the blood pump 100 such that the cannula 204 is at least partially positioned in the left ventricle of the subject. At block 308, the method 300 further includes manipulating the pull wire 218 to modify the shape profile of the cannula 204 after the cannula 204 has crossed the aortic valve, as well. In this way, there is a continuing ability for the physician to control the desired positioning and configuration of the cannula 204 throughout the delivery and positioning of the blood pump 100 to ensure the blood inlets 110 are in a safe and effective location within the left ventricle.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The invention claimed is:

1. A percutaneous circulatory support device, comprising:
- a housing comprising an outlet;
- an impeller disposed within the housing and being rotatable relative to the housing to cause blood to flow through the housing and out of the outlet;
- a cannula coupled to the housing, the cannula having a body extending between a proximal end and a distal end and along a longitudinal axis, a structural body portion, a surface coating disposed onto the structural body portion of the cannula, and a channel defined between the structural body portion of the cannula and the surface coating;
- a pull wire coupled to the cannula and extending through the channel of the cannula; and
- wherein manipulation of the pull wire causes a change in a shape profile of the cannula body.

2. The percutaneous circulatory support device of claim 1, wherein the device comprises two pull wires.

3. The percutaneous circulatory support device of claim 2, wherein the cannula body is defined by a longitudinal axis, and the two pull wires are coupled to the cannula body on opposing sides of the cannula body relative to the longitudinal axis.

4. The percutaneous circulatory support device of claim 1, wherein the surface coating is composed of a polymer coating.

5. The percutaneous circulatory support device of claim 1, wherein the pull wire is composed of nitinol.

6. The percutaneous circulatory support device of claim 1, wherein the pull wire comprises a radiopaque coating.

7. The percutaneous circulatory support device of claim 1, wherein the cannula body is formed of a plurality of wires in a braided configuration.

8. The percutaneous circulatory support device of claim 1, wherein the body of the cannula is composed of a plurality of wires in a helical configuration.

9. The percutaneous circulatory support device of claim 1, wherein manipulation of the pull wire causes the cannula body to have a curved profile.

10. The percutaneous circulatory support device of claim 9, wherein the manipulation of the pull wire includes retracting the pull wire in a proximal direction.

11. The percutaneous circulatory support device of claim 1, wherein the channel is positioned on an interior surface of the structural body portion.

12. The percutaneous circulatory support device of claim 1, wherein the channel is positioned on an exterior surface of the structural body portion.

13. A percutaneous circulatory support device, comprising:
- a housing;
- an impeller disposed within the housing and being rotatable relative to the housing;
- a cannula coupled to the housing, the cannula having a body extending between a proximal end and a distal end along a longitudinal axis;
- a first pull wire coupled to the body of the cannula on a first side of the cannula;
- a second pull wire coupled to the body of the cannula on a second side of the cannula; and
- wherein the body of the cannula comprises a structural body portion and a surface coating disposed on the structural body portion;
- wherein the first pull wire is disposed radially between the structural body portion and the surface coating, and the second pull wire is disposed radially between the structural body portion and the surface coating;
- wherein manipulation of the first or second pull wires causes a change in configuration of the cannula body.

14. The percutaneous circulatory support device of claim 13, wherein the first side is opposite the second side relative to the longitudinal axis.

15. The percutaneous circulatory support device of claim 13, wherein the cannula comprises a channel defined between the structural body portion and the surface coating configured to receive at least one pull wire.

16. A method for positioning a blood pump within a subject, the method comprising:
- advancing the blood pump through the vasculature of the subject, wherein the blood pump comprises a cannula having a body extending along a longitudinal axis and a pull wire coupled to the body, wherein the pull wire is disposed radially between a structural body portion of the body and a surface coating disposed on the structural body portion of the body;
- manipulating the pull wire to cause a change in a shape profile of the cannula;

crossing the aortic valve of the subject with the blood pump such that the cannula is at least partially positioned in the left ventricle of the subject; and manipulating the pull wire to cause a change in a shape of the cannula body.

17. The method of claim 16, wherein manipulating the pull wire includes retracting the pull wire in a proximal direction.

18. The method of claim 16, wherein prior to the manipulating of the pull wire, the cannula body extends along the longitudinal axis.

19. The method of claim 18, wherein after the manipulating of the pull wire, the cannula body comprises a curved profile.

* * * * *